US006958398B1

(12) United States Patent
Kupper et al.

(10) Patent No.: US 6,958,398 B1
(45) Date of Patent: Oct. 25, 2005

(54) METHODS FOR MAKING THEBAINE OR ITS ACID SALTS

(75) Inventors: Robert J. Kupper, East Greenwich, RI (US); Arie Gutman, Haifa (IL); Igor Rukhman, Haifa (IL); Lev Yudovich, Haifa (IL); Gennady A. Nisnevich, Haifa (IL)

(73) Assignee: Euro-Celtique S.A., Luxembourg (LU)

( * ) Notice: Subject to any disclaimer, the term of this patent is extended or adjusted under 35 U.S.C. 154(b) by 88 days.

(21) Appl. No.: 10/722,054

(22) Filed: Nov. 25, 2003

Related U.S. Application Data

(60) Provisional application No. 60/436,657, filed on Dec. 30, 2002.

(51) Int. Cl.[7] ............................................. C07D 489/04
(52) U.S. Cl. ......................................................... 546/44
(58) Field of Search ........................................... 546/44

(56) References Cited

U.S. PATENT DOCUMENTS

| | | |
|---|---|---|
| 4,045,440 A | 8/1977 | Rapoport et al. |
| 6,090,943 A | 7/2000 | Mudryk et al. |

FOREIGN PATENT DOCUMENTS

GB        1260 699        1/1972

OTHER PUBLICATIONS

Choudhrey et al., 1989, "The Synthesis of Thebaine-1-$^3$H," J. Labell. Cmpd. Radiopharm. 27(12):1403-1408.
Coop et al., 1998, "A Novel Synthesis of Thebaine from Codeine," Heterocycles 49:43-47.
Rapoport et al., 1967, "The Synthesis of Thebaine and Northebaine from Codeinone Dimethyl Ketal," J. Amer. Chem. Soc. 89(8):1942-1947.
Seki et al., 1970, "Studies on the Morphine Alkaloids and Its Related Compounds. XVII. One-Step Preparations of Enol Ether and Pyrrolidinyl Dienamine of Normorphinone Derivatives," Chem. Pharm. Bull. 18(4):671-676.
The Merck Index, 2001, 13th ed., 9346.
Remington: The Science and Practice of Pharmacy, 2000, 20th ed., p. 1448.

*Primary Examiner*—Taofig Solola
(74) *Attorney, Agent, or Firm*—Jones Day

(57) ABSTRACT

Methods for making thebaine and an acid salt of thebaine are disclosed herein. In one embodiment, an acid salt of thebaine is made from codeinone or an acid salt of one or more of the following: 8-methoxy-$\Delta^6$-dihydrothebaine, codeinone dimethyl ketal, and neopinone dimethyl ketal.

49 Claims, No Drawings

METHODS FOR MAKING THEBAINE OR ITS ACID SALTS

This application claims the benefit of U.S. Provisional Application No. 60/436,657, filed Dec. 30, 2002, the entire disclosure being incorporated herein by reference.

1. FIELD OF THE INVENTION

The present invention relates to methods for making thebaine or its acid salts.

2. BACKGROUND OF THE INVENTION

Thebaine is an N-methylmorphinan having the structure:

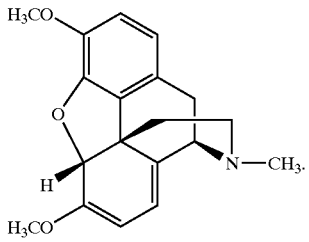

Thebaine or an acid salt thereof is an intermediate that is useful for making a variety of morphine alkaloids, in particular 14-hydroxymorphinans, such as oxycodone. Morphine alkaloids are useful for treating pain.

The following references describe processes for making thebaine:

U.S. Pat. No. 3,894,026 to Sohar et al. describes a method for preparing thebaine from salutarindol.

U.S. Pat. No. 4,045,440 to Rapaport et al. and R. Barber et al., *J. Med. Chem.* 18(11):1074–1077 (1975) describe a method for making thebaine by reacting codeine with potassium hydride and methyl iodide to provide the O-6 methyl ester of codeine, and then oxidizing the 0–6 methyl ester of codeine with $MnO_2$ in tetrahydrofuran.

U.S. Pat. No. 6,090,943 to Mudryk et al. describes a method for making thebaine by reacting codeinone with a metal alkoxide, such as potassium tert-butoxide, in a solvent that does not react with the codeinone or metal alkoxide, such as N-methylpyrrolidone, then reacting the resultant product with a methylating agent, such as dimethylsulfate.

D. H. R. Barton et al., *J. Chem. Soc.* 2423–2438 (1965) describes a synthesis of salutaridine and a method for converting it to thebaine.

H. Rapoport et al., *J. Amer. Chem. Soc.* 89(8):1942–1947 (1967) describes a method for making thebaine by reacting codeinone dimethyl ketal with phosphorous oxychloride in pyridine.

T. Kametani et al., *J. Chem. Soc.* (C) 2030–2033 (1969) describes a method for making thebaine by diazotizing (±)-1-(2-amino-3-benzyloxy-4-methoxybenzyl)-1,2,3,4-tetrahydro-6,7-dimethoxy-2-methylisoquinoline, thermally decomposing the resultant diazonium salt to provide (±)-salutaridine, and converting the (±)-salutaridine to thebaine.

M. Schwartz et al., *J. Amer. Chem. Soc.* 97(5):1239–1240 (1975) describes a method for making thebaine from N-trifluoroacetylnorreticuline and N-ethoxycarbonylnorreticuline.

A. Coop et al., *Heterocycles* 49:43–47 (1998) describes a method for making thebaine by reacting codeinone with potassium tert-butoxide in the presence of 18-Crown-6 and adding dimethyl sulfate.

Despite these described methods, there remains a need for improved methods for making thebaine and its acid salts.

Citation of any reference in Section 2 of this application is not an admission that the reference is prior art to the application.

3. SUMMARY OF THE INVENTION

The present invention relates to methods for making thebaine or its acid salts.

In one embodiment, the invention relates to a method for making thebaine, comprising the steps of:

(a) heating a reaction mixture comprising an acid salt of 8-methoxy-$\Delta^6$-dihydrothebaine and an acid at a temperature and for a time sufficient to make methanol and an acid salt of thebaine;

(b) distilling the methanol; and (c) neutralizing the acid salt of thebaine.

In another embodiment, the invention relates to a method for making thebaine, comprising the steps of:

(a) heating a reaction mixture comprising an acid salt of codeinone dimethyl ketal and an acid at a temperature and for a time sufficient to make methanol and an acid salt of thebaine;

(b) distilling the methanol; and (c) neutralizing the acid salt of thebaine.

In another embodiment, the invention relates to a method for making thebaine, comprising the steps of:

(a) heating a reaction mixture comprising an acid salt of neopinone dimethyl ketal and an acid at a temperature and for a time sufficient to make methanol and an acid salt of thebaine;

(b) distilling the methanol; and (c) neutralizing the acid salt of thebaine.

In another embodiment, the invention relates to a method for making thebaine, comprising the steps of:

(a) heating a first reaction mixture comprising an acid salt of codeinone, trimethyl orthoformate, methanol and an acid at about the reaction mixture's boiling point to provide a second reaction mixture;

(b) distilling substantially all of the methanol from the second reaction mixture to provide a third reaction mixture;

(c) heating the third reaction mixture at a temperature and for a time sufficient to make methanol and an acid salt of thebaine; and (d) neutralizing the acid salt of thebaine.

The present invention can be understood more fully by reference to the following detailed description and illustrative examples, which exemplify non-limiting embodiments of the invention.

4. DETAILED DESCRIPTION OF THE INVENTION

The present invention relates to methods for making thebaine or its acid salts.

4.1 Definitions

"8-Methoxy-Δ$^6$-dihydrothebaine" has the structure of formula (I):

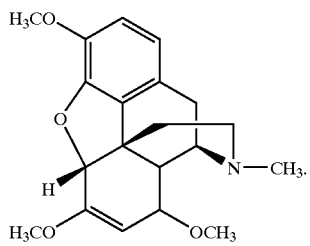

"Codeinone dimethyl ketal" has the structure of formula (II):

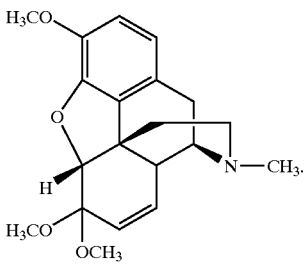

"Neopinone dimethyl ketal" has the structure of formula (III):

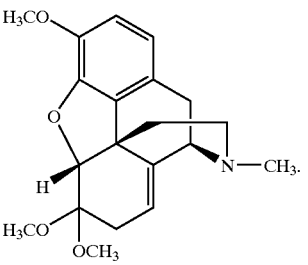

The phrase "distilling substantially all of the methanol," as used herein in connection with a reaction mixture means distilling at least about 90 percent of the methanol from the reaction mixture; in one embodiment, at least about 95 percent of the methanol from the reaction mixture; in another embodiment, at least about 98 percent of the methanol from the reaction mixture; and in another embodiment, at least about 99 percent of the methanol from the reaction mixture.

The phrase "substantially anhydrous," as used herein in connection with a reaction mixture means that the reaction mixture comprises less than about 1 percent of water by weight; in one embodiment, less than about 0.5 percent of water by weight; and in another embodiment, less than about 0.25 percent of water by weight of the reaction mixture.

The phrases "acid salt of 8-methoxy-Δ$^6$-dihydrothebaine," "acid salt of codeinone dimethyl ketal," "acid salt of neopinone dimethyl ketal," "acid salt of thebaine" and "acid salt of codeinone" as used herein, mean a salt formed from an acid and the basic nitrogen group of 8-methoxy-Δ$^6$-dihydrothebaine, codeinone dimethyl ketal, neopinone dimethyl ketal, thebaine, or codeinone, respectively.

The phrase "xylene," as used herein means p-xylene, o-xylene, m-xylene, or a mixture thereof.

4.2 Methods for Making Thebaine or an Acid Salt Thereof

The invention relates to methods for making thebaine or an acid salt thereof from a reaction mixture comprising an acid salt of one or more of the following: 8-methoxy-Δ$^6$-dihydrothebaine, codeinone dimethyl ketal, neopinone dimethyl ketal (an acid salt of each of the foregoing being a "Thebaine Precursor") and codeinone.

4.2.1 Methods Comprising Heating a Reaction Mixture Comprising a Thebaine Precursor and an Acid In one embodiment, a method for making thebaine comprises the steps of (a) heating a reaction mixture comprising an acid salt of 8-methoxy-Δ 6-dihydrothebaine and an acid at a temperature and for a time sufficient to make methanol and an acid salt of thebaine; (b) distilling the methanol; and (c) neutralizing the acid salt of thebaine. In another embodiment, the reaction mixture comprises an acid salt of 8-methoxy-Δ$^6$-dihydrothebaine, an acid salt of codeinone dimethyl ketal, and an acid. In yet another embodiment, the reaction mixture further an acid salt of 8-methoxy-Δ$^6$-dihydrothebaine, an acid salt of neopinone dimethyl ketal, and an acid. In still another embodiment, the reaction mixture comprises an acid salt of an acid salt of 8-methoxy-Δ$^6$-dihydrothebaine, an acid salt of codeinone dimethyl ketal, an acid salt of neopinone dimethyl ketal, and an acid. In still another embodiment, the reaction mixture comprises an acid salt of codeinone dimethyl ketal, an acid salt of neopinone dimethyl ketal, and an acid.

In another embodiment, a method for making thebaine comprises the steps of (a) heating a reaction mixture comprising an acid salt of codeinone dimethyl ketal and an acid at a temperature and for a time sufficient to make methanol and an acid salt of thebaine; (b) distilling the methanol; and (c) neutralizing the acid salt of thebaine. In another embodiment, the reaction mixture further comprises an acid salt of neopinone dimethyl ketal.

In another embodiment, a method for making thebaine comprises the steps of (a) heating a reaction mixture comprising an acid salt of neopinone dimethyl ketal and an acid at a temperature and for a time sufficient to make methanol and an acid salt of thebaine; (b) distilling the methanol; and (c) neutralizing the acid salt of thebaine.

In one embodiment, the reaction mixture is heated until at least about 95 mole percent of the total amount of the Thebaine Precursor(s) in the reaction mixture is converted to the acid salt of thebaine. In another embodiment, the reaction mixture is heated until at least about 97 mole percent of the total amount of the Thebaine Precursor(s) in the reaction mixture is converted to the acid salt of thebaine. In another embodiment, the reaction mixture is heated until at least about 99 mole percent of the total amount of the Thebaine Precursor(s) in the reaction mixture is converted to the acid salt of thebaine. The conversion of a Thebaine Precursor to an acid salt of thebaine can be monitored using conventional analytical techniques, including, but are not limited to, thin-layer chromatography ("TLC"), high-performance liquid chromatography ("HPLC"), gas chromatography ("GC"), and nuclear magnetic resonance spectroscopy ("NMR") such as $^1$H or $^{13}$C NMR.

Typically, heating the reaction mixture for a time of about 0.25 hour to about 20 hours is an amount of time sufficient to make methanol; in another embodiment, a time of about 1 hour to about 10 hours is a time sufficient to make methanol; and in another embodiment, a time of about 2 hours to about 6 hours is an amount of time sufficient to make methanol.

Typically, about 85° C. to about 120° C. is a temperature that is sufficient to make methanol; in another embodiment, about 90° C. to about 110° C. is a temperature that is sufficient to make methanol; and in another embodiment, about 95° C. to about 100° C. is a temperature that is sufficient to make methanol.

In one embodiment, the acid is present in the reaction mixture in an amount ranging from about 0.01 to about 10 molar equivalents relative to the total amount of the Thebaine Precursor(s); in another embodiment, the acid is present in the reaction mixture in an amount ranging from about 0.01 to about 5 molar equivalents relative to the total amount of the Thebaine Precursor(s); and in another embodiment, the acid is present in the reaction mixture in an amount ranging from about 0.01 to about 2 molar equivalents relative to the total amount of the Thebaine Precursor(s).

Suitable acids for use in the methods of the invention include, but are not limited to, hydrochloric acid, hydrobromic acid, hydroiodic acid, hydrofluoric acid, sulfuric acid, perchloric acid, nitric acid, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, and mixtures thereof. In one embodiment, the acid is benzenesulfonic acid, p-toluenesulfonic acid, p-bromobenzenesulfonic acid, p-nitrobenzenesulfonic acid, p-trifluoromethylbenzenesulfonic acid, methanesulfonic acid, ethanesulfonic acid, and trifluoromethanesulfonic acid. In one embodiment, the acid is methanesulfonic acid.

In one embodiment, the reaction mixture further comprises a solvent. Suitable solvents for use in the methods of the invention include those that dissolve or suspend a component of the reaction mixture. In one embodiment, the solvent is non-nucleophilic. In another embodiment, the solvent is non-alcoholic. Suitable solvents include, but are not limited to, toluene, benzene, xylene, heptane, tetrahydrofuran, dimethylformamide, dimethylsulfoxide, acetonitrile, carbon tetrachloride, chloroform, methylene chloride, and ligroin.

In one embodiment, a Thebaine Precursor(s) is dissolved or suspended in a solvent. When the Thebaine Precursor(s) is dissolved or suspended in the solvent, the concentration of the Thebaine Precursor(s) in the solvent typically ranges from about 0.01 moles to about 3 moles per liter of solvent. In one embodiment, the concentration of the Thebaine Precursor(s) in the solvent ranges from about 0.05 moles to about 1 mole per liter of solvent. In another embodiment, the concentration of the Thebaine Precursor(s) in the solvent ranges from about 0.1 moles to about 0.5 moles per liter of solvent.

In one embodiment, the reaction mixture comprises a solvent that forms an azeotrope with methanol. Examples of solvents that form an azeotrope with methanol include, but are not limited to, toluene, benzene, xylene, heptane, acetone, acetonitrile, 2,5-dimethylfuran, ethylbutyl ether, methyl acetate, nitromethane, octane, trichloroethylene, and 1,1,2-trichlorotrifluoroethane. In one embodiment, the solvent that forms an azeotrope with methanol is toluene, benzene, xylene, or heptane. In another embodiment, the solvent that forms an azeotrope with methanol is toluene.

In one embodiment, the methanol is distilled at atmospheric pressure. In another embodiment, the methanol is distilled under reduced pressure. In one embodiment, the methanol is distilled from the reaction mixture as an azeotrope comprising methanol and a solvent that forms an azeotrope with methanol.

Suitable Thebaine Precursors are salts of 8-methoxy-$\Delta^6$-dihydrothebaine, codeinone dimethyl ketal, neopinone dimethyl ketal. Suitable acid salts include, but are not limited to, methanesulfonate, ethanesulfonate, trifluoromethanesulfonate, benzenesulfonate, p-toluenesulfonate, p-bromobenzenesulfonate, p-nitrobenzenesulfonate, p-trifluoromethylbenzenesulfonate, chloride, bromide, iodide, fluoride, sulfate, citrate, acetate, oxalate, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, and pamoate (i.e., 1,1'-methylene-bis-(2-hydroxy-3-naphthoate)) salts. In one embodiment, the acid salt is a methanesulfonate, ethanesulfonate, trifluoromethanesulfonate, benzenesulfonate, p-toluenesulfonate, p-bromobenzenesulfonate, p-nitrobenzenesulfonate, or p-trifluoromethylbenzenesulfonate salt. In one embodiment, the acid salt is a methanesulfonate salt.

Neutralizing the acid salt of thebaine is accomplished by deprotonating the acid salt of thebaine. One skilled in the art would know how to neutralize an acid salt of thebaine. Typically, thebaine is obtained from an acid salt of thebaine by contacting the acid salt of thebaine with any suitable base. Suitable bases include, but are not limited to, alkali earth and alkaline earth metal hydroxides, such as LiOH, NaOH, KOH, RbOH, CsOH, FrOH, Be(OH)$_2$, Mg(OH)$_2$, Ca(OH)$_2$, Sr(OH)$_2$, Ba(OH)$_2$, and Ra(OH)$_2$ and alkali earth and alkaline earth metal alkoxides, such as LiOR, NaOR, KOR, RbOR, CsOR, FrOR, Be(OR)$_2$, Mg(OR)$_2$, Ca(OR)$_2$, Sr(OR)$_2$, Ba(OR)$_2$, and Ra(OR)$_2$, wherein R is an -alkyl group such as, but not limited to, -methyl, -ethyl, -n-butyl, -t-butyl, or -isopropyl. Sufficient base is added to the acid salt of thebaine to convert it to thebaine. Typically, the acid salt of thebaine is contacted with at least about 1 equivalent of base relative to the amount of the acid salt of thebaine. In one embodiment, the acid salt of thebaine is contacted with about 1.1 equivalents of base relative to the amount of the acid salt of thebaine. In another embodiment, the acid salt of thebaine is contacted with about 1.2 equivalents of base relative to the amount of the acid salt of thebaine.

In one embodiment, the acid salt of thebaine and the base are contacted in an aqueous or alcoholic solvent. In one embodiment, the base is in an aqueous solution and the acid salt of thebaine is in an aqueous solvent, such as water, methanol:water or ethanol:water; in this embodiment, the thebaine precipitates from the solvent. The thebaine can be collected, for example, using filtration. In one embodiment, the aqueous solution of the base is between about 20% and 30% aqueous NaOH. In another embodiment, the aqueous solution of the base is 25% aqueous NaOH. In another embodiment, sufficient base is added to an aqueous mixture of the acid salt of thebaine so that the resulting pH of the aqueous solution is about 11 or higher. In another embodiment, sufficient base is added to an aqueous mixture of the acid salt of thebaine so that the resulting pH of the aqueous solution is about 11. In another embodiment, sufficient base is added to an aqueous mixture of the acid salt of thebaine so that the resulting pH of the aqueous solution is about 12 or higher. In another embodiment, sufficient base is added to an aqueous mixture of the acid salt of thebaine so that the resulting pH of the aqueous solution is about 12.

In one embodiment, the acid salt of thebaine is neutralized by diluting it with dimethyl formamide and water, allowing the resulting mixture to stir for at least about 30 minutes, and then separating the resulting organic phase and aqueous phase. The aqueous phase is then cooled to a temperature of about 0° C. to about 5° C., and the pH of the aqueous phase is adjusted to a value of at least about 10 to provide a slurry of thebaine that is stirred at a temperature of about 0° C. to about 5° C. for at least about 1 hour. The slurry of thebaine is then filtered and the solid thebaine washed with deionized water until the filtrate is about pH-neutral. The thebaine is then dried. In one embodiment, the amount of dimethyl formamide is about 1 molar equivalent relative to the amount of the acid salt of thebaine, and the amount of water is about 85 equivalents relative to the amount of the acid salt of thebaine. The pH of the aqueous phase can be adjusted by adding a base to the aqueous phase. Suitable bases for adjusting the pH of the aqueous phase to a value of at least about 10 include, but are not limited to, those described above. In one embodiment, an aqueous solution of the base is added to the aqueous phase. In one embodiment, the pH of the aqueous phase is adjusted using a 25% aqueous solution of NaOH. In one embodiment, the pH of the aqueous phase is adjusted to a pH value of at least about 11. In another embodiment, the pH of the aqueous phase is adjusted to a pH value of at least about 12. Once obtained, the thebaine can be dried, optionally under reduced pressure, at a temperature ranging from about 25° C. to about 60° C., or from about 30° C. to about 55° C., or from about 45° C. to about 50° C.

The thebaine can be isolated and purified. As used herein, "isolated" means that the thebaine is separated from other components of a reaction mixture. As used herein, "purified" means that when isolated, the isolate contains at least about 90 percent of thebaine by weight of the isolate. In one embodiment, the isolate contains at least about 95 percent of thebaine by weight of the isolate. In another embodiment, the isolate contains at least about 97 percent of thebaine by weight of the isolate. Isolation and purification can be achieved using procedures well known to those skilled in the art including, for example, but not limited to, extraction, recrystallization, column chromatography, sublimation, preparative TLC, preparative HPLC, and preparative GC.

In one embodiment, thebaine is purified by recrystallizing it from a 1:1 mixture of water:iso-propanol. In another embodiment, the thebaine is purified by recrystallizing it from a 1:1 mixture of water:iso-propanol and then washing the thebaine with a 3:1 mixture of water:iso-propanol.

Typically, the overall yield of the isolated and purified thebaine is greater than about 70 percent based on the amount of the Thebaine Precursor(s) or codeinone. In one embodiment, the overall yield of the isolated and purified thebaine is greater than about 75 percent based on the amount of the Thebaine Precursor(s) or codeinone starting material. In another embodiment, the overall yield of the isolated and purified thebaine is greater than about 80 percent based on the amount of the Thebaine Precursor(s) or codeinone.

4.2.2 Methods Comprising Heating a Reaction Mixture Comprising an Acid Salt of Codeinone, Trimethyl Orthoformate, Methanol and an Acid The invention still further relates to a method for making thebaine, comprising the steps of (a) heating a first reaction mixture comprising an acid salt of codeinone, trimethyl orthoformate, methanol, and an acid at about the reaction mixture's boiling point to provide a second reaction mixture; (b) distilling substantially all of the methanol from the second reaction mixture to provide a third reaction mixture; (c) heating the third reaction mixture at a temperature and for a time sufficient to make methanol and an acid salt of thebaine; and (d) neutralizing the acid salt of thebaine.

The concentration of the acid salt of codeinone in the first reaction mixture typically ranges from about 0.01 moles to about 3 moles per liter of the first reaction mixture. In one embodiment, the concentration of the acid salt of codeinone in the first reaction mixture ranges from about 0.05 moles to about 1 mole per liter of the first reaction mixture. In another embodiment, the concentration of the acid salt of codeinone in the first reaction mixture ranges from about 0.1 mole to about 0.5 moles per liter of the first reaction mixture.

The amount of trimethyl orthoformate in the first reaction mixture is typically at least about a 1.5-fold molar excess relative to the amount of the acid salt of codeinone. In one embodiment, the amount of trimethyl orthoformate in the first reaction mixture is at least about a 2-fold molar excess relative to the amount of the acid salt of codeinone. In another embodiment, the amount of trimethyl orthoformate in the first reaction mixture is at least about a 3-fold molar excess relative to the amount of the acid salt of codeinone.

The amount of acid in the first reaction mixture typically ranges from about 0.01 to about 11 molar equivalents relative to the acid salt of codeinone. In another embodiment, the amount of acid in the first reaction mixture ranges from about 0.01 to about 6 molar equivalents relative to the acid salt of codeinone. In another embodiment, the amount of acid in the first reaction mixture ranges from about 0.01 to about 3 molar equivalents relative to the acid salt of codeinone. In another embodiment, the amount of acid in the first reaction mixture ranges from about 1.0 to about 1.5 molar equivalents relative to the acid salt of codeinone. Suitable acids for use in the method of making the acid salt of thebaine from the acid salt of codeinone include, but are not limited to, those described above.

The amount of methanol in the first reaction mixture is typically at least about 10 molar equivalents relative to the acid salt of codeinone. In one embodiment, the methanol is present in the first reaction mixture in an amount that is at least about 20 molar equivalents relative to the acid salt of codeinone. In another embodiment, the methanol is present in the first reaction mixture in an amount that is at least about 30 molar equivalents relative to the acid salt of codeinone. In another embodiment, the methanol is present in the first reaction mixture in an amount that is at least about 40 molar equivalents relative to the acid salt of codeinone. In one embodiment, the methanol is present in the first reaction mixture in an amount that ranges from about a 10 molar equivalents to about 1,000 molar equivalents relative to the acid salt of codeinone. In another embodiment, the methanol is present in the first reaction mixture in an amount that ranges from about a 20 molar equivalents to about 1,000 molar equivalents relative to the acid salt of codeinone. In another embodiment, the methanol is present in the first reaction mixture in an amount that ranges from about a 30 molar equivalents to about 1,000 molar equivalents relative to the acid salt of codeinone. In another embodiment, the methanol is present in the first reaction mixture in an amount that ranges from about a 40 molar equivalents to about 1,000 molar equivalents relative to the acid salt of codeinone.

In one embodiment, the first reaction mixture is heated for an amount of time sufficient to provide a second reaction mixture that comprises at least one Thebaine Precursor. Typically, the first reaction mixture is heated for an amount of time sufficient to provide a second reaction mixture having an amount of the acid salt of codeinone that has decreased by at least about 85 percent of its original amount. In one embodiment, the amount of time is sufficient to provide a second reaction mixture having an amount of the acid salt of codeinone that has decreased by at least about 90 percent of its original amount. In another embodiment, the amount of time is sufficient to provide a second reaction mixture having an amount of the acid salt of codeinone that has decreased by at least about 93 percent of its original amount. The progress of the reaction can be monitored using conventional analytical techniques, including, but are not limited to, any of those described above.

Typically, the first reaction mixture is heated for a time period ranging from about 1 hour to about 20 hours. In one embodiment, the first reaction mixture is heated for a time period ranging from about 1 hour to about 10 hours. In another embodiment, the first reaction mixture is heated for a time period ranging from about 2 hours to 6 hours.

Typically, the first reaction mixture is heated at a temperature ranging from about 30° C. to about 150° C. In another embodiment, the first reaction mixture is heated at a temperature ranging from about 40° C. to about 150° C. In another embodiment, the first reaction mixture is heated at a temperature ranging from about 50° C. to about 150° C. In another embodiment, the first reaction mixture is heated at a temperature ranging from about 60° C. to about 68° C.

In one embodiment, the first reaction mixture further comprises a solvent. Suitable solvents include, but are not limited to, those described above.

In one embodiment, the first reaction mixture is substantially anhydrous.

In one embodiment, the methanol is distilled from the second reaction mixture at atmospheric pressure. In another embodiment, the methanol is distilled from the second reaction mixture under reduced pressure. In another embodiment, the methanol is distilled from the second reaction mixture as an azeotrope comprising methanol and a solvent that forms an azeotrope with methanol. Suitable solvents that form an azeotrope with methanol include, but are not limited to, those described above. In one embodiment, the methanol is removed by distilling an azeotrope comprising methanol and toluene, methanol and benzene, methanol and xylene, or methanol and heptane. In another embodiment, the methanol is removed by distilling an azeotrope comprising methanol and toluene.

Typically, heating the third reaction mixture for about 1 hour to about 20 hours is an amount of time sufficient to make methanol and an acid salt of thebaine. In one embodiment, anywhere from about 1 hour to about 10 hours, and in another embodiment, anywhere from about 2 hours to about 6 hours, is an amount of time sufficient to make methanol and an acid salt of thebaine.

Typically, about 85° C. to about 120° C. is a temperature range sufficient to make methanol and an acid salt of thebaine from the third reaction mixture. In another embodiment, about 90° C. to about 110° C., and in another embodiment, about 55° C. to about 100° C., are temperature ranges sufficient to make methanol and an acid salt of thebaine from the third reaction mixture.

The acid salt of thebaine can be neutralized as described above.

The thebaine can be isolated and purified as described above.

4.3 Methods for Making Thebaine Precursors and their Acid Salts

The Thebaine Precursors used in the methods of the invention are prepared by protonating the nitrogen atom of 8-methoxy-$\Delta^6$-dihydrothebaine, codeinone dimethyl ketal or neopinone dimethyl ketal. One skilled in the art would know how to make an acid salt of 8-methoxy-$\Delta^6$-dihydrothebaine, codeinone dimethyl ketal or neopinone dimethyl ketal. Typically, the nitrogen atom of 8-methoxy-$\Delta^6$-dihydrothebaine, codeinone dimethyl ketal or neopinone dimethyl ketal is protonated by contacting it with an acid. In one embodiment, 8-methoxy-$\Delta$6-dihydrothebaine, codeinone dimethyl ketal or neopinone dimethyl ketal is in the presence of a solvent when it is contacted with the acid.

Suitable acids useful for making a Thebaine Precursor are any that protonate the nitrogen atom of 8-methoxy-$\Delta^6$-dihydrothebaine, codeinone dimethyl ketal or neopinone dimethyl ketal. Such acids include, but are not limited to, methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylbenzenesulfonic acid, hydrochloric acid, hydrobromic acid, hydroiodic acid, hydrofluoric acid, sulfuric acid, citric acid, acetic acid, oxalic acid, nitric acid, phosphoric acid, isonicotinic acid, lactic acid, salicylic acid, tartaric acid, oleic acid, tannic acid, pantothenic acid, ascorbic acid, succinic acid, maleic acid, gentisinic acid, fumaric acid, gluconic acid, glucaronic acid, saccharic acid, formic acid, benzoic acid, glutamic acid, and pamoic acid (i.e., 1,1'-methylene-bis-(2-hydroxy-3-naphthoic acid), among others.

A representative procedure for making 8-methoxy-$\Delta^6$-dihydrothebaine and codeinone dimethyl ketal is described in H. Rapoport et al., *J. Amer. Chem. Soc.*, 89(8): 1942–1947 (1967).

A representative procedure for making neopinone dimethyl ketal is described in Dauben et al., *J. Org. Chem.*, 44: 1567 (1979).

In one embodiment, a mixture of the acid salt of 8-methoxy-$\Delta^6$-dihydrothebaine, the acid salt of codeinone dimethyl ketal and the acid salt of neopinone dimethyl ketal can be obtained by admixing about 1 molar equivalent of codeinone with about 2 molar equivalents of trimethyl orthoformate, from about 5 to about 100 molar equivalents of methanol, from about 1 to about 2 molar equivalents of methanesulfonic acid and about 5 to about 50 molar equivalents of toluene and heating the resulting mixture at a temperature in a range of about 50° C. to about 80° C., in one embodiment in a range of about 55° C. to about 75° C., in another embodiment in a range of about 60° C. to about 70° C., and in another embodiment in a range of about 62° C. to 64° C., for a time period ranging from about 1 to about 6 hours, in another embodiment for a time period ranging from about 2 to about 5 hours, and in another embodiment for a time period ranging from about 3 hours to about 4 hours.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, fall within the scope of the present invention.

5. EXAMPLES

5.1 Example 1

Synthesis of Thebaine from Codeinone

To a dried 4-neck 5-liter round bottom flask equipped with a mechanical stirrer, heating mantle, pressure equalizing dropping funnel, and reflux condenser under a nitrogen atmosphere were added 100 g of codeinone, 500 mL of methanol and 73.5 mL of trimethyl orthoformate. The resulting mixture was allowed to stir at room temperature. Methanesulfonic acid (42 g) was then added to the flask at a temperature of about 25° C. over a time period of about 10 minutes. After addition of the methanesulfonic acid, 500 mL of toluene was added and the resulting mixture was allowed to reflux for about 4 to 6 h. at a temperature of about 62° C. to about 64° C. until HPLC analysis using a reverse phase C-18 silica gel column eluted with a gradient of 25:75 acetonitrile:water to 50:50 acetonitrile:water showed that at least 93% of the codeinone was consumed. The reflux condenser was replaced with a distillation apparatus, the mixture was heated at a temperature of from about 91° C. to about 93° C. and methanol was allowed to distill from the reaction mixture until substantially all the methanol was removed. At various intervals an aliquot of the reaction mixture was removed, quenched in a phosphate buffer solution having a pH value of about 8, and analyzed using HPLC. The reaction mixture was monitored hourly until HPLC analysis showed that the peak corresponding to thebaine was at least about 95 percent of the total peak area (about 3 to 4 h). Dimethylformamide (22.4 mL) was then added to the reaction mixture and the reaction mixture was allowed to cool to room temperature. The reaction mixture was then quenched with an equal volume of deionized water and allowed to stir for about 30 minutes. The aqueous and organic phases were allowed to separate. The aqueous phase was then cooled to a temperature of from about 0° to about 5° C. and allowed to stir vigorously, and 25% aqueous sodium hydroxide was added until the pH of the resulting slurry was about 12. The resulting slurry was stirred at about 0° C. for at least about 1 h and then filtered. The resulting solid was washed with deionized water until the pH of the filtrate was neutral (3×50 mL) to provide a wet cake of thebaine (150 g). The wet cake of thebaine was dried under reduced pressure (40 mm Hg) at a temperature of from about 45° to about 50° C. for about 16 h to provide dry thebaine (85 g).

5.2 Example 2

Synthesis of Thebaine from Codeinone

To a dried 4-neck 5-liter round bottom flask equipped with a mechanical stirrer, heating mantle, pressure equalizing dropping funnel, and reflux condenser under a nitrogen atmosphere were added 100 g of codeinone, 500 mL of methanol and 73.5 mL of trimethyl orthoformate. The resulting mixture was allowed to stir at a temperature of from about 10° to about 15° C. Methanesulfonic acid (42 g) was then added to the flask at a temperature of about 10° C. to about 20° C. over a time period of about 10 minutes. To the resultant solution was added 500 mL of toluene, and the resulting mixture was allowed to reflux for about 3 h at a temperature of about 62° C. to about 64° C. until at least 93% of the codeinone was consumed. The reflux condenser was replaced with a distillation apparatus, the mixture was heated at a temperature of from about 91° C. to about 93° C., and methanol was allowed to distill from the reaction mixture until substantially all the methanol was removed. At various intervals an aliquot of the reaction mixture was removed, quenched in a phosphate buffer solution having a pH value of about 8, and analyzed using HPLC. The reaction mixture was monitored hourly until HPLC analysis showed that the peak corresponding to thebaine was at least about 95 percent of the total peak area (about 3 to 4 h). Dimethylformamide (22.4 mL) was then added to the reaction mixture, and the reaction mixture was heated at a temperature of from about 90° C. to about 95° C. for from about 3 to about 4 h. The mixture was cooled to about 25° C., deionized distilled water (500 mL) was added, and the resultant biphasic mixture was stirred at 25° C. for 0.5 h. The aqueous phase was collected, and to it was added iso-propanol (166 mL). The resultant mixture was heated to reflux, and treated with 25% NaOH (120 mL). The resultant slurry was slowly cooled with stirring to about 25° C. then further cooled to 0° C. to 5° C. and filtered. The solid was then washed with 3×50 mL of 3:1 (v:v) deionized distilled water:iso-propanol and dried under reduced pressure (40 mm Hg) at a temperature of from about 45° to about 50° C. for about 16 h to provide dry thebaine (67–80 g) as an off-white solid.

5.3 Example 3

Purification of Thebaine

The thebaine made and isolated in Example 1 was further purified by dissolving it in about 320 mL of 1:1 deionized water:iso-propanol, stirring the resultant mixture at room temperature for about 1 h, heating the mixture to about 65° C., adding about 160 mL of deionized water to the mixture, heating the resultant mixture at about 65° C. for about 1 h, cooling the mixture to about room temperature, and stirring the mixture at about room temperature for about 1 h to provide a precipitate. The precipitate was collected by filtration and was washed with a 3:1 mixture of water:iso-propanol (3×100 mL). The washed precipitate was then dried under reduced pressure at a temperature of from about 45° to about 50° C. for about 16 h to provide purified thebaine (80 g) as an off-white solid. The purity of the thebaine was greater than 97% by HPLC analysis (reverse phase C-18 silica gel column eluted with a gradient of 25:75 acetonitrile:water to 50:50 acetonitrile:water).

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited herein, the entire disclosures of which are incorporated herein by reference in their entireties.

What is claimed is:

1. A method for making thebaine, comprising the steps of:
   (a) heating a reaction mixture comprising an acid salt of 8-methoxy-$\Delta^6$-dihydrothebaine and an acid at a temperature and for a time sufficient to make methanol and an acid salt of thebaine;
   (b) distilling the methanol; and
   (c) neutralizing the acid salt of thebaine with a base.

2. The method of claim 1, wherein the acid is present in an amount of about 0.01 to about 10 molar equivalents relative to the amount of the acid salt of 8-methoxy-$\Delta^6$-dihydrothebaine.

3. The method of claim 1, wherein the temperature is from about 85° C. to about 120° C.

4. The method of claim 1, wherein the time is from about 1 hour to about 20 hours.

5. The method of claim 1, wherein the acid is methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylsulfonic acid.

6. The method of claim 1, wherein the reaction mixture further comprises a solvent.

7. The method of claim 6, wherein the concentration of the acid salt of 8-methoxy-$\Delta^6$-dihydrothebaine is from about 0.01 moles to about 3 moles per liter of solvent.

8. The method of claim 1, wherein the base is aqueous sodium hydroxide.

9. The method of claim 6, wherein the solvent forms an azeotrope with methanol.

10. The method of claim 9, wherein the solvent is selected from the group consisting of toluene, benzene, xylene, heptane, acetone, 2,5-dimethylfuran, ethylbutyl ether, methyl acetate, nitromethane, octane, trichloroethylene, and 1,1,2-trichlorotrifluoroethane.

11. The method of claim 1, wherein the reaction mixture further comprises an acid salt of codeinone dimethyl ketal.

12. The method of claim 11, wherein the acid is present in an amount of about 0.01 to about 10 molar equivalents relative to the total amount of the acid salt of 8-methoxy-$\Delta^6$-dihydrothebaine and the acid salt of codeinone dimethyl ketal.

13. The method of claim 1, wherein the reaction mixture further comprises an acid salt of neopinone dimethyl ketal.

14. The method of claim 13, wherein the acid is present in an amount of about 0.01 to about 10 molar equivalents relative to the total amount of the acid salt of 8-methoxy-$\Delta^6$-dihydrothebaine and the acid salt of neopinone dimethyl ketal.

15. The method of claim 11, wherein the reaction mixture further comprises an acid salt of neopinone dimethyl ketal.

16. The method of claim 15, wherein the acid is present in an amount of about 0.01 to about 10 molar equivalents relative to the total amount of the acid salt of 8-methoxy-$\Delta^6$-dihydrothebaine, the acid salt of codeinone dimethyl ketal, and the acid salt of neopinone dimethyl ketal.

17. A method for making thebaine comprising the steps of:
   (a) heating a reaction mixture comprising an acid salt of codeinone dimethyl ketal and an acid at a temperature and for a time sufficient to make methanol and an acid salt of thebaine;
   (b) distilling the methanol; and
   (c) neutralizing the acid salt of thebaine with a base.

18. The method of claim 17, wherein the acid is present in an amount of about 0.01 to about 10 molar equivalents relative to the amount of the acid salt of codeinone dimethyl ketal.

19. The method of claim 17, wherein the temperature is from about 85° C. to about 120° C.

20. The method of claim 17, wherein the time is from about 1 hour to about 20 hours.

21. The method of claim 17, wherein the acid is methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylsulfonic acid.

22. The method of claim 17, wherein the reaction mixture further comprises a solvent.

23. The method of claim 22, wherein the concentration of acid salt of codeinone dimethyl ketal is from about 0.01 moles to about 3 moles per liter of solvent.

24. The method of claim 17, wherein the base is aqueous sodium hydroxide.

25. The method of claim 22, wherein the solvent forms an azeotrope with methanol.

26. The method of claim 25, wherein the solvent is selected from the group consisting of toluene, benzene, xylene, heptane, acetone, 2,5-dimethylfuran, ethylbutyl ether, methyl acetate, nitromethane, octane, trichloroethylene, and 1,1,2-trichlorotrifluoroethane.

27. The method of claim 17, wherein the reaction mixture further comprises an acid salt of neopinone dimethyl ketal.

28. The method of claim 27, wherein the acid is present in an amount of about 0.01 to about 10 molar equivalents relative to the total amount of the acid salt of 8-methoxy-$\Delta^6$-dihydrothebaine and the acid salt of codeinone dimethyl ketal.

29. A method for making thebaine comprising the steps of:
   (a) heating a reaction mixture comprising an acid salt of neopinone dimethyl ketal and an acid at a temperature and for a time sufficient to make methanol and an acid salt of thebaine;
   (b) distilling the methanol; and
   (c) neutralizing the acid salt of thebaine.

30. The method of claim 29, wherein the acid is present in an amount of about 0.01 to about 10 molar equivalents relative to the amount of the acid salt of neopinone dimethyl ketal.

31. The method of claim 29, wherein the temperature is from about 85° C. to about 120° C.

32. The method of claim 29, wherein the time is from about 1 hour to about 20 hours.

33. The method of claim 29, wherein the acid is methanesulfonic acid, ethanesulfonic acid, trifluoromethanesulfonic acid, benzenesulfonic acid, p-toluenesulfonic acid, p-bromobenzenesulfonic acid, p-nitrobenzenesulfonic acid, p-trifluoromethylsulfonic acid.

34. The method of claim 29, wherein the reaction mixture further comprises a solvent.

35. The method of claim 34, wherein the concentration of the acid salt of neopinone dimethyl ketal is from about 0.01 moles to about 3 moles per liter of solvent.

36. The method of claim 29, wherein the base is aqueous sodium hydroxide.

37. The method of claim 34, wherein the solvent forms an azeotrope with methanol.

38. The method of claim 37, wherein the solvent is selected from the group consisting of toluene, benzene, xylene, heptane, acetone, 2,5-dimethylfuran, ethylbutyl ether, methyl acetate, nitromethane, octane, trichloroethylene, and 1,1,2-trichlorotrifluoroethane.

39. A method for making thebaine comprising the steps of:
(a) heating a first reaction mixture comprising an acid salt of codeinone, trimethyl orthoformate, methanol, and an acid at about the reaction mixture's boiling point to provide a second reaction mixture;
(b) distilling substantially all of the methanol from the second reaction mixture to provide a third reaction mixture;
(c) heating the third reaction mixture at a temperature and for a time sufficient to make methanol and an acid salt of thebaine; and
(d) neutralizing the acid salt of thebaine with a base.

40. The method of claim 1, wherein the third reaction mixture is heated at a temperature of from about 85° C. to about 120° C.

41. The method of claim 39, wherein the amount of the acid salt of codeinone in the first reaction mixture is from about 0.01 moles to about 3 moles per liter of the reaction mixture.

42. The method of claim 39, wherein the amount of the trimethyl orthoformate in the first reaction mixture is at least about a 1.5 fold molar excess relative to the amount of the acid salt of codeinone.

43. The method of claim 39, wherein the amount of the acid in the first reaction mixture is from about 0.1 to about 10 molar equivalents relative to the amount of the acid salt of codeinone.

44. The method of claim 39, wherein the amount of the methanol in the first reaction mixture is at least about 10 molar equivalents relative to the amount of the acid salt of codeinone.

45. The method of claim 39, wherein the third reaction mixture is heated for a time of from about 1 hour to about 20 hours.

46. The method of claim 39, wherein the first reaction mixture is substantially anhydrous.

47. The method of claim 39, wherein the first reaction mixture further comprises a solvent.

48. The method of claim 40, wherein the methanol distilled in step (b) is a component of a methanol-solvent azeotrope.

49. The method of claim 48, wherein the solvent that forms an azeotrope with methanol is selected from the group consisting of toluene, benzene, xylene, heptane, acetone, acetonitrile, 2,5-dimethylfuran, ethylbutyl ether, methyl acetate, nitromethane, octane, trichloroethylene, and 1,1,2-trichlorotrifluoroethane.

* * * * *